US012590051B2

(12) United States Patent
Sakuma et al.

(10) Patent No.: US 12,590,051 B2
(45) Date of Patent: Mar. 31, 2026

(54) METHOD FOR PRODUCING BINAPHTHYL CARBOXYLIC ACID

(71) Applicant: HONSHU CHEMICAL INDUSTRY CO., LTD., Tokyo (JP)

(72) Inventors: Daichi Sakuma, Wakayama (JP); Takeru Suto, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 884 days.

(21) Appl. No.: 17/771,433

(22) PCT Filed: Nov. 26, 2020

(86) PCT No.: PCT/JP2020/044037

§ 371 (c)(1),
(2) Date: Apr. 22, 2022

(87) PCT Pub. No.: WO2021/107016

PCT Pub. Date: Jun. 3, 2021

(65) Prior Publication Data

US 2023/0002300 A1 Jan. 5, 2023

(30) Foreign Application Priority Data

Nov. 29, 2019 (JP) ................................ 2019-216304

(51) Int. Cl.
*C07C 51/09* (2006.01)

(52) U.S. Cl.
CPC .................................. *C07C 51/09* (2013.01)

(58) Field of Classification Search
None
See application file for complete search history.

(56) References Cited

U.S. PATENT DOCUMENTS

| | | | | |
|---|---|---|---|---|
| 2020/0354299 A1 | | 11/2020 | Reuter et al. | |
| 2022/0396544 A1 | * | 12/2022 | Kodera | C07C 59/31 |

FOREIGN PATENT DOCUMENTS

| | | | | | |
|---|---|---|---|---|---|
| EP | 3805195 A1 | * | 4/2021 | | C07C 51/43 |
| EP | 3967677 A1 | * | 3/2022 | | C07C 51/09 |
| EP | 4067334 A1 | | 10/2022 | | |
| JP | 2008024650 A | | 2/2008 | | |
| JP | 2018002893 A | | 1/2018 | | |
| JP | 2018002894 A | | 1/2018 | | |
| JP | 2018002895 A | | 1/2018 | | |
| WO | WO-2019043060 A1 | * | 3/2019 | | C07C 43/23 |
| WO | WO-2019230685 A1 | * | 12/2019 | | C07C 51/43 |
| WO | WO-2020226114 A1 | * | 11/2020 | | C07C 51/09 |

OTHER PUBLICATIONS

Ghosh et al., (rac)-1,1'-Binaphthyl-based simple receptors designed for fluorometric discrimination of maleic and fumaric acid, The Journal of Physical Chemistry B, 2011, pp. 8597-8608, vol. 115, No. 26. (12 pages).
International Search Report (ISR) mailed Jan. 12, 2021, issued for International application No. PCT/JP2020/044037. (2 pages).
Lehn et al., Synthesis and properties of chiral macrotricyclic ligands. Complexation and transport of chiral molecular cations and anions, Helvetica Chimica Acta, 1978, pp. 2407-2418, vol. 61, No. 7. (12 pages).
A First Office Action issued by the State Intellectual Property Office of China on Jul. 1, 2023, for Chinese counterpart application No. 202080074002.9 (6 pages).
Fengying et al., Synthesis of 1, 1'-Bi-2, 2'-naphthol Diether, Journal of Sun Yat-sen University, Natural Science Edition, May 1996, 120-123, vol. 35, No. 3 (4 pages).
International Preliminary Report on Patentability, dated May 17, 2022, for corresponding international application PCT/JP2020/044037 (1 page).
Notification Concerning Transmittal of International Preliminary Report on Patentability, mailed Jun. 9, 2022, for corresponding international application PCT/JP2020/044037 (1 page).
Notification of Transmittal of Translation of the International Preliminary Report on Patentability, mailed Jun. 9, 2022, for corresponding international application PCT/JP2020/044037 (1 page).
Written Opinion of the International Searching Authority, mailed Jan. 12, 2021, for corresponding international application PCT/JP2020/044037 (3 page).
Extended European Search Report (EESR) dated Dec. 1, 2023, issued for European counterpart patent application No. EP20894468.6 (10 pages).

* cited by examiner

*Primary Examiner* — Amy C Bonaparte
(74) *Attorney, Agent, or Firm* — Law Office of Katsuhiro Arai

(57) ABSTRACT

A method for producing 2,2'-bis(carboxymethoxy)-1,1'-binaphthyl includes performing steps (i) to (iv) below in sequence using a 2,2'-bis(alkoxycarbonylmethoxy)-1,1'-binaphthyl as a starting material:
(i) a hydrolysis reaction step,
(ii) a step of distilling off a resulting alcohol represented by formula (3) above from a reaction system,
(iii) a step of acidifying a reaction solution, and
(iv) a step of precipitating 2,2'-bis(carboxymethoxy)-1,1'-binaphthyl in the presence of an organic solvent.

2 Claims, No Drawings

METHOD FOR PRODUCING BINAPHTHYL CARBOXYLIC ACID

CROSS-REFERENCE TO RELATED APPLICATIONS

This application is the U.S. National Phase under 35 U.S.C. § 371 of International Application PCT/JP2020/044037, filed Nov. 26, 2020, which claims priority to Japanese Patent Application No. JP2019-216304, filed Nov. 29, 2019. The International Application was published under PCT Article 21 (2) in a language other than English.

TECHNICAL FIELD

The present invention relates to a method for producing a binaphthyl carboxylic acid.

BACKGROUND ART

Polyester resins and polyester carbonate resins produced using dicarboxylic acid components having a binaphthalene skeleton as polymerization components have excellent optical properties such as high refractive indices and low birefringence and have high levels of heat resistance, and thus have recently been expected to be materials for optical members such as optical disks, transparent conductive substrates, and optical filters. In particular, resins produced using 2,2'-bis(carboxymethoxy)-1,1'-binaphthyl, which has a chemical structure represented by a chemical formula below, as a polymerization component have been attracting attention for their particularly excellent optical properties (see, for example, PTLs 1 to 3).

[Chem. 1]

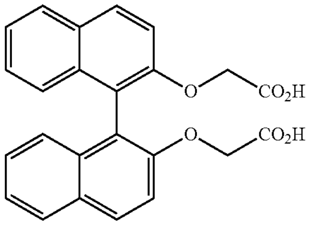

Known methods for producing 2,2'-bis(carboxymethoxy)-1,1'-binaphthyl represented by the above chemical formula include reaction of 1,1'-binaphthalene-2,2'-diol with a halogenated acetate ester, as shown by a reaction formula below, and hydrolysis of a diester obtained by the reaction.

[Chem. 2]

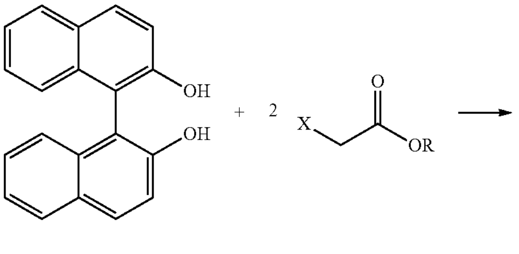

-continued

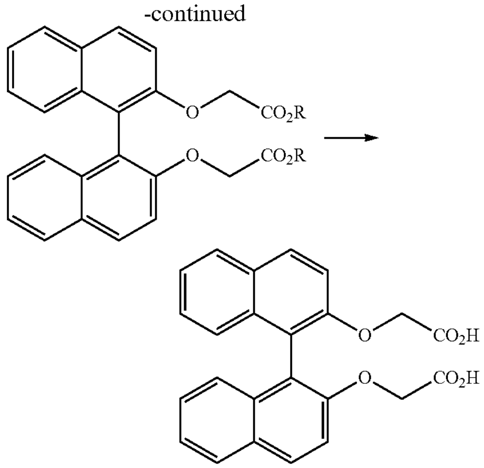

The present inventors have focused for the first time on the fact that if an alcohol is contained in a reaction solution when the reaction solution is acidified after the above hydrolysis reaction, a carboxylic acid of 2,2'-bis(carboxymethoxy)-1,1'-binaphthyl reacts with the alcohol to produce an ester, resulting in decreases in the yield and purity of 2,2'-bis(carboxymethoxy)-1,1'-binaphthyl.

CITATION LIST

Patent Literature

PTL 1: Japanese Unexamined Patent Application Publication No. 2018-002893

PTL 2: Japanese Unexamined Patent Application Publication No. 2018-002894

PTL 3: Japanese Unexamined Patent Application Publication No. 2018-002895

SUMMARY OF INVENTION

Technical Problem

An object of the present invention is to provide a production method that can provide highly pure 2,2'-bis(carboxymethoxy)-1,1'-binaphthyl.

Solution to Problem

To achieve the above object, the present inventors have conducted intensive studies and discovered that highly pure 2,2'-bis(carboxymethoxy)-1,1'-binaphthyl can be obtained in a manner that after a hydrolysis reaction, an ester-derived alcohol is distilled off from the reaction system, then the reaction solution is acidified, and 2,2'-bis(carboxymethoxy)-1,1'-binaphthyl is precipitated in the presence of an organic solvent, thereby completing the present invention.

The present invention is as follows.

1. A method for producing 2,2'-bis(carboxymethoxy)-1,1'-binaphthyl represented by formula (2) below, including performing steps (i) to (iv) below in sequence using a 2,2'-bis(alkoxycarbonylmethoxy)-1,1'-binaphthyl represented by formula (1) below as a starting material:

(i) a hydrolysis reaction step, (ii) a step of distilling off a resulting alcohol represented by formula (3) below from a reaction system, (iii) a step of acidifying a reaction solution, and (iv) a step of precipitating 2,2'-bis(carboxymethoxy)-1,1'-binaphthyl in the presence of an organic solvent.

[Chem. 3]

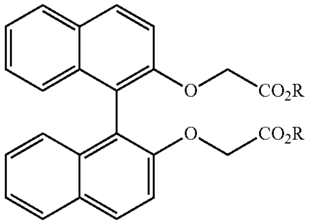

(1)

(In the formula, each R independently represents an alkyl group having 1 to 8 carbon atoms.)

[Chem. 4]

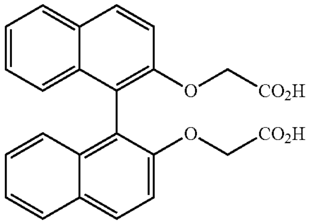

(2)

[Chem. 5]

ROH (3)

(In the formula, R represents an alkyl group having 1 to 8 carbon atoms.)

2. The method for producing 2,2'-bis(carboxymethoxy)-1,1'-binaphthyl according to 1., including a reaction step of reacting 1,1'-binaphthalene-2,2'-diol with a halogenated acetate ester represented by formula (4) below to obtain the 2,2'-bis(alkoxycarbonylmethoxy)-1,1'-binaphthyl represented by formula (1).

[Chem. 6]

$XCH_2COOR$ (4)

(In the formula, X represents a halogen atom, and R represents an alkyl group having 1 to 8 carbon atoms.)

Advantageous Effects of Invention

According to the present invention, the problem of the traditional hydrolysis reaction in that an ester-derived alcohol and 2,2'-bis(carboxymethoxy)-1,1'-binaphthyl react with each other to produce an ester, resulting in a decrease in purity, is overcome, and highly pure 2,2'-bis(carboxymethoxy)-1,1'-binaphthyl can be obtained.

The provision of the production method of the present invention is very useful in industrial production of resin raw materials and the like because highly pure 2,2'-bis(carboxymethoxy)-1,1'-binaphthyl can be obtained.

DESCRIPTION OF EMBODIMENTS

Hereinafter, the present invention will be described in detail.

The production method of the present invention is a method represented by the reaction formula below and includes performing the above steps (i) to (iv) in sequence in one and the same reaction vessel. Hereinafter, a 2,2'-bis(alkoxycarbonylmethoxy)-1,1'-binaphthyl represented by formula (1) below is referred to as a "diester (1)", 2,2'-bis(carboxymethoxy)-1,1'-binaphthyl represented by formula (2) below as "Target A", and an alcohol represented by formula (3) below as an "alcohol".

[Chem. 7]

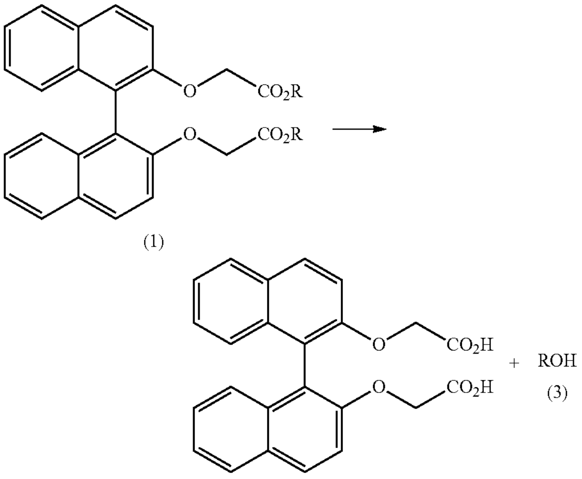

(1) (2) (3)

(In the formula, each R independently represents an alkyl group having 1 to 8 carbon atoms.)

<Reaction step of Obtaining Diester (1)>

The "diester (1)" in the present invention can be obtained by reacting 1,1'-binaphthalene-2,2'-diol and a halogenated acetate ester represented by formula (4) below (hereinafter also referred to as the "ester (4)") with each other, as shown by the reaction formula below.

[Chem. 8]

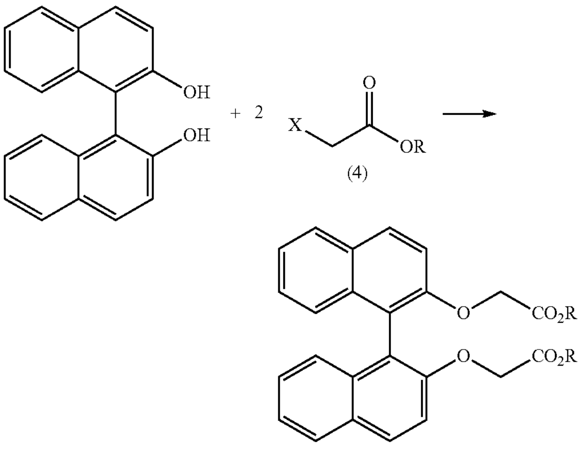

(4) (1)

(In the formula, each R independently represents an alkyl group having 1 to 8 carbon atoms.)

(Ester (4))

"R" in the formula of the ester (4) used to synthesize the diester (1) is an alkyl group having 1 to 8 carbon atoms, and specific examples include linear alkyl groups such as a methyl group, an ethyl group, and a n-propyl group, and branched alkyl groups in which the carbon bonded to an oxygen atom is primary or secondary carbon, such as an i-propyl group and an i-butyl group. Among them, alkyl groups having 1 to 3 carbon atoms are preferred, and linear alkyl groups are more preferred. Likewise, "X" in the formula is a halogen atom, preferably a chlorine atom, a bromine atom, or an iodine atom.

In the synthesis of the diester (1), two or more esters (4) having different alkyl ester moieties may be used in combination, but for simple and easy purification, it is preferable to use a single ester (4).

The amount of the ester (4) used is not particularly limited as long as the molar ratio of the ester (4) to 1,1'-binaphthalene-2,2'-diol is more than or equal to a theoretical value (2.0), and the ester (4) is typically used in an amount of 2 mol or more, preferably in an amount of 2.1 to 3.0 mol, more preferably in an amount of 2.2 to 2.8 mol.

(Reaction Solvent)

The synthesis of the diester (1) may be performed without a reaction solvent but is preferably performed using a reaction solvent for reasons of, for example, ease of operation in industrial production and improvement in reaction rate. The reaction solvent is not particularly limited as long as it is not distilled out of the reaction vessel at a reaction temperature and is inactive in the reaction, and examples include linear or cyclic ketone solvents having 5 to 8 carbon atoms, such as diethyl ketone, methyl isobutyl ketone, methyl amyl ketone, 2-octanone, cyclopentanone, and cyclohexanone; and linear nitrile solvents having 2 to 6 carbon atoms, such as acetonitrile and propanenitrile. These reaction solvents may be used alone or may be used in an appropriate combination of two or more to adjust polarity. In particular, methyl isobutyl ketone and acetonitrile are preferred.

The amount of reaction solvent used is preferably in the range of 150 to 500 parts by weight, more preferably in the range of 200 to 300 parts by weight, relative to 100 parts by weight of 1,1'-binaphthalene-2,2'-diol.

(Base)

In the synthesis of the diester (1), 1,1'-binaphthalene-2,2'-diol is preferably formed into a salt with a base before being reacted with the ester (4). The base is not particularly limited, and, for example, alkali metal carbonates such as lithium carbonate, sodium carbonate, and potassium carbonate; alkali metal hydrogen carbonates such as sodium hydrogen carbonate and potassium hydrogen carbonate; alkali metal hydroxides such as lithium hydroxide, sodium hydroxide, and potassium hydroxide; and organic bases such as triethylamine and pyridine are suitable for use. These may be used alone or as a mixture of two or more. In particular, sodium carbonate and potassium carbonate are preferred.

The amount of base used is preferably 2.0 to 2.5 mol, more preferably 2.05 to 2.15 mol, relative to 1 mol of 1,1'-binaphthalene-2,2'-diol.

(Alkali Metal Iodide)

In the synthesis of the diester (1), the reaction may be carried out in the presence of an alkali metal iodide. Specific examples of alkali metal iodides include potassium iodide, sodium iodide, cesium iodide, and lithium iodide. These may be used alone or as a mixture of two or more.

The amount of alkali metal iodide used is preferably in the range of 1 to 25 mol %, more preferably in the range of 2 to 15 mol %, still more preferably in the range of 2.5 to 10 mol %, particularly preferably in the range of 3 to 5 mol %, relative to 1 mol of 1,1'-binaphthalene-2,2'-diol.

(Reaction Temperature and Pressure)

The reaction temperature is typically 50° C. to 150° C., preferably in the range of 70° C. to 130° C., more preferably in the range of 90° C. to 110° C. A high reaction temperature is not preferred because the yield decreases due to, for example, hydrolysis of the resulting diester (1), and a low reaction temperature is not preferred because the reaction rate slows down. The reaction is typically carried out under normal pressure, but depending on the boiling point of an organic solvent used, the reaction may be carried out under pressure or reduced pressure so that the reaction temperature falls within the above range.

(Reaction Endpoint)

The endpoint of the reaction can be determined by liquid chromatography or gas chromatography analysis. The endpoint of the reaction is preferably defined as the time point at which unreacted 1,1'-binaphthalene-2,2'-diol has disappeared and the increase of the diester (1) is no longer observed. Although the reaction time varies depending on the reaction conditions such as reaction temperature, the reaction is typically completed in about 1 to 30 hours.

After completion of the reaction, water is added to the reaction solution, the mixture is stirred, and the resultant is then left to stand to separate an aqueous layer. This water washing operation is performed twice or more, whereby the inorganic salt in the reaction solution can be removed. The amount of water used in one water washing operation is preferably in the range of 150 to 600 parts by weight, more preferably in the range of 200 to 400 parts by weight, relative to 100 parts by weight of 1,1'-binaphthalene-2,2'-diol used, and the temperature in the operation is preferably in the range of 60° C. to 100° C., more preferably in the range of 70° C. to 90° C. The stirring may be performed in any manner as long as an oil layer is sufficiently brought into contact with an aqueous layer, and although the time required varies depending on the apparatus, about 30 minutes usually suffices.

<(i) Hydrolysis Reaction Step>

(Reaction Solvent)

"(i) The hydrolysis reaction step" in the present invention can be performed, for example, using a solution that has been through the water washing operation after completion of the synthesis reaction of the diester (1). When "(i) the hydrolysis reaction step" of the present invention is performed using the diester (1) that has been purified, it is preferable to use a mixed solvent of an organic solvent and water as a reaction solvent. Specific examples of the organic solvent used include linear or cyclic ketone solvents having 5 to 8 carbon atoms, such as diethyl ketone, methyl isobutyl ketone, methyl amyl ketone, 2-octanone, cyclopentanone, and cyclohexanone; and linear nitrile solvents having 2 to 6 carbon atoms, such as acetonitrile and propanenitrile. The amount of organic solvent used is preferably 100 to 600 parts by weight, more preferably 130 to 400 parts by weight, relative to 100 parts by weight of the diester (1). The amount of water used is preferably 10 to 200 parts by weight, more preferably 20 to 150 parts by weight, relative to 100 parts by weight of the diester (1).

(Base)

To hydrolyze the diester (1), a base is used. Specific examples of the base used include alkali metal hydroxides such as lithium hydroxide, sodium hydroxide, and potassium hydroxide, and by using such a base, an alkali metal salt can be obtained as a metal salt (2). The base may be used as a solid or in the form of an aqueous solution. The concentration of the base used in the form of an aqueous solution is preferably 10 to 60 wt %, more preferably 20 to 50 wt %.

The amount of the base used is preferably 2.0 to 6.0 mol, more preferably 2.5 to 4.0 mol, relative to 1 mol of the diester (1).

(Reaction Temperature)

The reaction temperature is typically 30° C. to 100° C., preferably in the range of 50° C. to 90° C., more preferably in the range of 60° C. to 80° C., and it is preferable to add or drop the above base or an aqueous solution thereof while maintain this temperature.

The reaction is typically completed in about 1 to 10 hours.

<(ii) Step of Distilling Off Resulting Alcohol Represented by Formula (3) from Reaction System>

The production method of the present invention includes, after (i) the hydrolysis reaction step, a step of distilling off the "alcohol" resulting from the hydrolysis reaction from the reaction system.

(Temperature)

The temperature at which the "alcohol" is distilled off from the reaction system is preferably in the range of 40° C. to 130° C., more preferably in the range of 60° C. to 100° C., still more preferably in the range of 70° C. to 90° C.

(Pressure)

The pressure at which the "alcohol" is distilled off from the reaction system may be normal pressure or reduced pressure, and when the distillation is performed on an industrial scale, it is preferably performed under reduced pressure because the solvent can be distilled out more efficiently.

(Solvent)

When the "alcohol" is distilled off from the reaction system, an organic solvent may be added to the reaction system as required. Examples of the solvent added include linear ketone solvents having a total of 5 to 8 carbon atoms, such as diethyl ketone, methyl isobutyl ketone, methyl amyl ketone, methyl hexyl ketone, and 2-octanone.

(Distillation Quantity)

In distilling off the "alcohol" from the reaction system, the distillation quantity of the "alcohol" and the organic solvent added to the reaction system as required is preferably in the range of 150 to 450 parts by weight, more preferably 200 to 300 parts by weight, relative to 100 parts by weight of the diester (1).

<(iii) Step of Acidifying Reaction Solution>

The production method of the present invention includes, after (ii) the step of distilling off the resulting alcohol represented by formula (3) from the reaction system, a step of acidifying the reaction solution. Specific examples of an acid used in the step of acidifying the reaction solution include inorganic acids such as hydrogen chloride, hydrogen bromide, and sulfuric acid, and organic acids such as p-toluenesulfonic acid, methanesulfonic acid, and trifluoromethanesulfonic acid. The amount of acid used is preferably 2.2 to 4.0 mol, more preferably 2.5 to 3.0 mol, relative to 1 mol of the diester (1).

When concentrated hydrochloric acid is used as the acid, the amount thereof in terms of hydrogen chloride is preferably 2.2 to 4.0 mol, more preferably 2.5 to 3.0 mol, relative to 1 mol of the diester (1).

Specific examples of a reaction solvent in the step of acidifying the reaction solution include linear or cyclic ketone solvents having 5 to 8 carbon atoms, such as diethyl ketone, methyl isobutyl ketone, methyl amyl ketone, 2-octanone, cyclopentanone, and cyclohexanone. The amount of reaction solvent used is preferably 250 to 1050 parts by weight, more preferably 350 to 900 parts by weight, relative to 100 parts by weight of the diester (1).

<(iv) Step of Precipitating 2,2'-bis(carboxymethoxy)-1,1'-binaphthyl in Presence of Organic Solvent>

The production method of the present invention includes, after (iii) the step of acidifying the reaction solution, a step of precipitating Target A in the presence of an organic solvent. After (iii) the step of acidifying the reaction solution, the reaction solution is preferably washed with water before (iv) the step of precipitating Target A is performed. More preferably, the reaction solution is washed with water once to multiple times to the extent that an aqueous layer left after the water washing operation becomes neutral to slightly acidic. In the step (iv) of the production method of the present invention, 2,2'-bis(carboxymethoxy)-1,1'-binaphthyl is preferably crystallized in the presence of an organic solvent.

(Solvent)

The step of precipitating Target A is performed in the presence of at least an organic solvent. The precipitation may be performed not only in the presence of an organic solvent but also in the presence of a mixture of an organic solvent and water, and, in particular, it is preferable to precipitate Target A in the presence of a mixed solvent of water and (a) at least one selected from linear ketone solvents having a total of 5 to 8 carbon atoms, (b) at least one selected from cyclic ketone solvents having a total of 5 to 8 carbon atoms, (c) at least one selected from cyclic ether solvents having a total of 4 to 8 carbon atoms, (d) at least one selected from cyclic ester solvents having a total of 4 to 8 carbon atoms, or (e) at least one selected from linear ketone solvents having a total of 3 to 8 carbon atoms or in the presence of any of these solvents (a) to (e). Of these, methyl isobutyl ketone, methyl amyl ketone, and 2-octanone, which have low water solubility, are suitable, and the amount of linear ketone solvent used to dissolve Target A is preferably 250 to 1000 parts by weight, more preferably 300 to 800 parts by weight, still more preferably 400 to 600 parts by weight, relative to 100 parts by weight of Target A contained in crystals or a solution used. The amount of cyclic ketone solvent, cyclic ether solvent, or cyclic ester solvent used to dissolve Target A is preferably 50 to 600 parts by weight, more preferably 50 to 400 parts by weight, still more preferably 100 to 200 parts by weight, relative to 100 parts by weight of Target A contained in crystals or a solution used.

(Temperature)

The temperature at which Target A is precipitated, for example, in the case where methyl isobutyl ketone, methyl amyl ketone, 2-octanone, or the like is used is preferably 90° C. to 130° C., more preferably 95° C. to 105° C.

A solution obtained by dissolving Target A in an organic solvent may be cooled as it is to precipitate Target A, or crystals may be precipitated while distilling out the organic solvent from the solution by distillation. The time spent on solvent distillation is preferably 2 to 15 hours, more preferably 4 to 10 hours, still more preferably 6 to 8 hours.

In the step of precipitating Target A, it is preferable to perform cooling after crystals are precipitated or while precipitating crystals, and the rate of the cooling is preferably 5° C. to 15° C. per hour, more preferably 7° C. to 12° C. per hour. In precipitating crystals, seed crystals need not be used but are preferably used, and crystals precipitated without seed crystals may be used as seed crystals. The final cooling temperature is preferably 20° C. to 60° C., more preferably 25° C. to 35° C. After cooling to this temperature, precipitated crystals are separated by filtration.

<Drying>

In the production method of the present invention, the crystals obtained by (iv) the step of precipitating Target A is preferably dried. By drying the crystals, the solvent used in (iv) the step of precipitating Target A can be removed. This drying can be performed by drying the crystals obtained by crystallization preferably under reduced pressure at 60° C. to 120° C., more preferably under reduced pressure at 70° C. to 110° C. The drying may be performed under normal pressure or reduced pressure. When the drying is performed on an industrial scale, it is preferably performed under reduced pressure because the solvent used in (iv) the step of precipitating Target A can be removed more efficiently.

EXAMPLES

The present invention will now be described more specifically with reference to Examples, but it should be noted that the present invention is not limited to these Examples.

The method of analysis is as follows.

<Method of Analysis>

1. Determination of Target A concentration in reaction solution, reaction yield, and reaction endpoint After the measurement was performed under the following conditions, the purity (%) of Targets A obtained in Examples and Comparative Examples was calculated using a liquid chromatography calibration curve of the target compound.

Measuring apparatus: high-performance liquid chromatography analyzer (manufactured by Shimadzu Corporation)

Pump: LC-20AD

Column oven: CTO-20A

Detector: SPD-20A

Column: HALO-C18

Oven temperature: 50° C.

Flow rate: 0.7 ml/min

Mobile phase: (A) acetonitrile, (B) 0.1 vol % aqueous phosphoric acid solution

Gradient conditions: (A) volume % (time from start of analysis)

30% (0 min)→100% (12 min)→100% (15 min)

Detection wavelength: 280 nm

Example 1

Production Method of Present Invention

In a four-necked flask, 300 g of 1,1'-binaphthalene-2,2'-diol, 750 g of methyl isobutyl ketone, 304.1 g of potassium carbonate, and 6.0 g of potassium iodide were placed, heated to 100° C., and stirred at this temperature for two hours. After the stirring, 300 g of methyl isobutyl ketone was distilled out under reduced pressure, and a mixed solution of 282.5 g of ethyl chloroacetate and 2.5 g of N-methylpyrrolidone was then prepared, after which the mixed solution was added dropwise while maintaining the temperature of the reaction solution at 90° C. to 100° C. After stirring for 10 hours, 2400 g of water was added, and the mixture was heated to 80° C. and then left to stand to remove an aqueous layer. After 900 g of methyl isobutyl ketone was added to the resulting oil layer, 261.9 g of a 48% aqueous sodium hydroxide solution was added dropwise while maintaining the temperature of the reaction solution at 80° C. to 85° C. (step (i)).

After stirring for two hours, 1200 g of methyl isobutyl ketone was added to the reaction solution, and 1200 g of methyl isobutyl ketone, ethanol, and water was distilled out under reduced pressure (final reduced pressure: 65 kPa) while maintaining the temperature of the reaction solution at 70° C. to 85° C. (step (ii)).

Water in an amount of 900 g and methyl isobutyl ketone in an amount of 1590 g were added, and 327.8 g of concentrated hydrochloric acid was added dropwise while maintaining the temperature at 80° C. to 85° C. The resultant was stirred at this temperature for 30 minutes (step (iii)). After standing, an aqueous layer was extracted, and a water washing operation involving addition of water to the resulting oil layer, stirring, and removal of an aqueous layer by separation was performed multiple times until the pH of the aqueous layer reached 4.

Subsequently, under normal pressure, 1954 g of water and methyl isobutyl ketone was distilled out of the resulting oil layer by distillation. At 95° C. midway through the distillation, seed crystals obtained by a production method known in the art were added, and precipitation of crystals was checked (step (iv)). The resultant was cooled to 30° C. at a cooling rate of 10° C. per hour, filtered, and then dried to obtain 385.3 g of a first crystallized crystalline body of Target A (yield: 91.4%, purity: 99.7%, monoethyl ester (a reaction product of one carboxylic acid of Target A and an alcohol): 0.2%).

(Crystallization of Target A)

In a four-necked flask, 30.0 g of the obtained crystalline body of Target A, 183.9 g of methyl isobutyl ketone, and 9.8 g of water were placed and heated to 85° C. to be dissolved. Subsequently, under normal pressure, 119.6 g of water and methyl isobutyl ketone was distilled out by distillation. At 95° C. midway through the distillation, seed crystals obtained by a production method known in the art were added, and precipitation of crystals was checked. After this, the crystallized solution was cooled to 25° C. at a cooling rate of 10° C. per hour, filtered, and then dried under reduced pressure to obtain 24.8 g of a second crystallized crystalline body of Target A (yield: 86.7%, purity: 99.9%, monoethyl ester: 0.08%).

Comparative Example 1

Production Method 1 Different from Production Method of Present Invention: Without Step (ii)

In a four-necked flask, 35 g of 1,1'-binaphthalene-2,2'-diol, 52.5 g of methyl isobutyl ketone, 35.5 g of potassium carbonate, and 0.7 g of potassium iodide were placed, heated to 100° C., and stirred at this temperature for two hours. After a mixed solution of 33.0 g of ethyl chloroacetate and 0.3 g of N-methylpyrrolidone was prepared, the mixed solution was added dropwise while maintaining the temperature of the reaction solution at 90° C. to 100° C. After stirring for 10 hours, 140 g of water was added, and the mixture was heated to 80° C., after which an aqueous layer was removed. Subsequently, 105.0 g of methyl isobutyl ketone was added, and 30.6 g of a 48% aqueous sodium hydroxide solution was added dropwise while maintaining the reaction solution temperature at 80° C. to 85° C. (step (i)).

After two hours, 185.5 g of methyl isobutyl ketone and 105.0 g of water were added to the reaction solution, after which 38.2 g of concentrated hydrochloric acid was added dropwise while maintaining the temperature at 80° C. to 85° C., and the resultant was stirred at this temperature for 30 minutes (step (iii)).

After standing, an aqueous layer was extracted, and a water washing operation involving addition of water to the resulting oil layer, stirring, and removal of an aqueous layer by separation was performed multiple times until the pH of the aqueous layer reached 4. Subsequently, under normal pressure, 231.6 g of water and methyl isobutyl ketone was distilled out of the resulting oil layer by distillation. At 95° C. midway through the distillation, seed crystals obtained by a production method known in the art were added, and precipitation of crystals was checked (step (iv)). After this, the solution in which crystals were precipitated was cooled to 25° C. at a cooling rate of 10° C. per hour and filtered to obtain 51.5 g of a first crystallized crystalline body of Target A (purity: 98.3%, monoethyl ester: 1.6%).

(Crystallization of Target A)

In a four-necked flask, 30.0 g of the obtained crystalline body of Target A, 183.9 g of methyl isobutyl ketone, and 9.8 g of water were placed and heated to 85° C. to be dissolved. Subsequently, under normal pressure, 119.6 g of water and methyl isobutyl ketone was distilled out by distillation. At 95° C. midway through the distillation, seed crystals obtained by a production method known in the art were added, and precipitation of crystals was checked. After this, the crystallized solution was cooled to 25° C. at a cooling rate of 10° C. per hour, filtered, and then dried under reduced pressure to obtain 24.8 g of a second crystallized crystalline body of Target A (yield: 86.4%, purity: 99.2%, monoethyl ester: 0.7%).

The first crystallized crystalline body of Example 1 has a purity of 99.7% and a monoethyl ester content of 0.2%. By contrast, the first crystallized crystalline body of Comparative Example 1 has a purity of 98.3% and a monoethyl ester content of 1.6%, and even the second crystallized crystalline body has a purity of 99.2% and a monoethyl ester content of 0.7%. These results have confirmed that the production method of the present invention including the step (ii) is an excellent production method that can provide highly pure 2,2'-bis(carboxymethoxy)-1,1'-binaphthyl.

Comparative Example 2

Production Method 2 Different from Production Method of Present Invention: Without Step (iv)

In 30 mL of a 20% sodium hydroxide solution in ethanol and water (ethanol:water=80:20, volume ratio), 1.0 g of 2,2'-bis(ethoxycarbonylmethoxy)-1,1'-binaphthyl was dissolved and refluxed for two hours (step (i)).

Ethanol was distilled out of the reaction solution, and the resultant was cooled (step (ii)).

Water was added to the resulting oil layer, and concentrated hydrochloric acid was used to adjust the pH to 1 (step (iii)).

Precipitated crystals were separated by filtration, dissolved in ethyl acetate, and dried over sodium sulfate, and the solvent was then distilled off to obtain Target A. According to calculations based on a peak area obtained by liquid chromatography, Target A obtained had a purity of 99.6% and a monoethyl ester content of 0.2%. The first crystallized crystalline body of Target A obtained in Example 1 had a purity of 99.95% and a monoethyl ester content of 0.02% according to calculations based on a peak area obtained by liquid chromatography.

The invention claimed is:

1. A method for producing 2,2'-bis(carboxymethoxy)-1,1'-binaphthyl represented by formula (2) below, comprising performing steps (i) to (iv) below in sequence using a 2,2'-bis(alkoxycarbonylmethoxy)-1,1'-binaphthyl represented by formula (1) below as a starting material:

(i) a hydrolysis reaction step, (ii) a step of distilling off a resulting alcohol represented by formula (3) below from a reaction system, (iii) a step of acidifying a reaction solution, and (iv) a step of precipitating 2,2'-bis(carboxymethoxy)-1,1'-binaphthyl in the presence of methyl isobutyl ketone as an organic solvent while cooling the reaction solution at a cooling rate of 5° C. to 15° C. per hour, wherein in step (i), a mixed solvent of methyl isobutyl ketone and water is used as a reaction solvent, and step (ii) comprises, after adding methyl isobutyl ketone to the reaction system, distilling off water and methyl isobutyl ketone together with the alcohol represented by formula (3) from the reaction system at a temperature of 70° C. to 90° C. under reduced pressure by a distillation quantity of 200 to 450 parts by weight, relative to 100 parts by weight of the 2,2'-bis(alkoxycarbonylmethoxy)-1,1'-binaphthyl represented by formula (1);

(1)

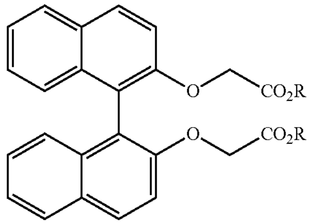

wherein each R independently represents an alkyl group having 1 to 8 carbon atoms, (2)

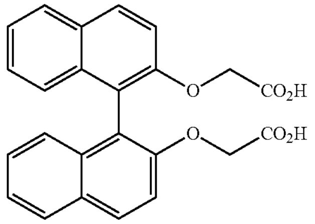

ROH (3)

wherein R represents an alkyl group having 1 to 8 carbon atoms.

2. The method for producing 2,2'-bis(carboxymethoxy)-1,1'-binaphthyl according to claim 1, comprising a reaction step of reacting 1,1'-binaphthalene-2,2'-diol with a halogenated acetate ester represented by formula (4) below to obtain the 2,2'-bis(alkoxycarbonylmethoxy)-1,1'-binaphthyl represented by formula (1), $XCH_2COOR$ (4)

wherein X represents a halogen atom, and R represents an alkyl group having 1 to 8 carbon atoms.

* * * * *